United States Patent
Moldenhauer

(10) Patent No.: US 11,206,784 B1
(45) Date of Patent: Dec. 28, 2021

(54) RICE CULTIVAR 'CLL16'

(71) Applicant: THE BOARD OF TRUSTEES OF THE UNIVERSITY OF ARKANSAS, Little Rock, AR (US)

(72) Inventor: Karen A. K. Moldenhauer, Stuttgart, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 16/903,625

(22) Filed: Jun. 17, 2020

(51) Int. Cl.
   *A01H 5/10* (2018.01)
   *A01H 6/46* (2018.01)

(52) U.S. Cl.
   CPC ............. *A01H 6/4636* (2018.05); *A01H 5/10* (2013.01)

(58) Field of Classification Search
   None
   See application file for complete search history.

(56) References Cited

U.S. PATENT DOCUMENTS 7,642,434 B2 * 1/2010 Moldenhauer ........... A01H 5/10
  800/320.2

* cited by examiner

*Primary Examiner* — Medina A Ibrahim
(74) *Attorney, Agent, or Firm* — Quarles & Brady LLP

(57) ABSTRACT

A rice cultivar designated CLL16 is disclosed herein. The present invention provides seeds, plants, and plant parts of or derived from rice cultivar CLL16. Further, it provides methods for producing a rice plant by crossing CLL16 with itself or another rice variety and methods for controlling weeds in the vicinity of a rice plant of rice cultivar CLL16 using an AHAS-inhibiting herbicide. The invention also encompasses any rice seeds, plants, and plant parts produced by the methods disclosed herein, including those in which additional traits have been transferred into CLL16 through the introduction of a transgene or by breeding CLL16 with another rice cultivar.

33 Claims, No Drawings

RICE CULTIVAR 'CLL16'

BACKGROUND OF THE INVENTION

The present invention relates to a new and distinctive rice cultivar, designated 'CLL16.' Rice is an ancient agricultural crop and is today one of the principal food crops of the world. There are two cultivated species of rice: *Oryza sativa* L., the Asian rice, and *O. glaberrima* Steud., the African rice. *O. sativa* L. constitutes virtually all of the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valleys of California.

Rice is a semi-aquatic crop that benefits from flooded soil conditions during part or all of the growing season. In the United States, rice is grown on flooded soils to optimize grain yields. Heavy clay soils or silt loam soils with hardpan layers about 30 cm below the surface are preferred rice-producing soils because they minimize water losses from soil percolation. Rice production in the United States can be broadly categorized as either dry-seeded or water-seeded. In the dry-seeded system, rice is sown into a well-prepared seedbed with a grain drill or by broadcasting the seed and incorporating it with a disk or harrow. Moisture for seed germination is provided by irrigation or rainfall. Alternatively, the seed may be broadcast by airplane into a flooded field, which is promptly drained following seeding. With the dry-seeded system, when the plants have reached sufficient size (four- to five-leaf stage), a shallow permanent flood of water, 5 to 16 cm deep, is applied to the field for the remainder of the crop season.

In the water-seeded system, rice seed is soaked for 12 to 36 hours to initiate germination, and the seed is broadcast by airplane into a flooded field. The seedlings emerge through a shallow flood, or the water may be drained from the field for a short period of time to enhance seedling establishment. A shallow flood is maintained until the rice approaches maturity. For both the dry-seeded and water-seeded production systems, the fields are drained when the crop is mature, and the rice is harvested 2 to 3 weeks later with large combines. In rice breeding programs, breeders typically employ the production systems predominant in their respective region. Thus, a drill-seeded breeding nursery is used by breeders in a region where rice is drill-seeded and a water-seeded nursery is used in regions where water-seeding is prominent.

Rice in the United States is classified into three primary market types by grain size, shape, and chemical composition of the endosperm: long-grain, medium-grain and short-grain. Typical U.S. long-grain cultivars cook dry and fluffy when steamed or boiled, whereas medium and short-grain cultivars cook moist and sticky. Traditionally, in the southern states, long-grain cultivars have been grown and generally receive higher market prices.

Rice, *Oryza sativa* L., is an important and valuable field crop. A continuing goal of plant breeders is to produce stable, high yielding rice cultivars that are agronomically sound. To accomplish this goal, rice plants with traits that result in superior cultivars must be developed.

SUMMARY OF THE INVENTION

The present invention provides a novel rice cultivar designated CLL16. The invention encompasses the seeds, plants, and plant parts of rice cultivar CLL16, as well as plants with essentially all of the physiological and morphological characteristics of CLL16.

In another aspect, the present invention provides methods for controlling weeds in the vicinity of a rice plant of rice cultivar CLL16 using an acetohydroxyacid synthase (AHAS)-inhibiting herbicide. In some embodiments, seeds of rice cultivar CLL16 are treated with an AHAS-inhibiting herbicide. In other embodiments, the herbicide is applied post-emergence.

This invention also provides methods for producing a rice plant by planting a plurality of seeds or by crossing rice CLL16 with itself or another rice line. Any plant breeding methods using rice cultivar CLL16 are part of this invention, including selfing, backcrosses, hybrid production, and crosses to populations. All plants and seeds produced using rice cultivar CLL16 as a parent are within the scope of this invention, including gene-converted plants of CLL16. Methods for introducing a gene into CLL16, either through traditional breeding, transformation or gene editing, are provided herein.

In still another aspect, the present invention provides regenerable cells for use in tissue culture of rice plant CLL16, as well as rice plants regenerated from these tissue cultures.

Definitions

To provide a clear and consistent understanding of the specification and claims, the following definitions are provided:

Allele. One of two or more alternative forms of a gene, all of which relate to a single trait or characteristic. In a diploid cell or organism, two alleles of a given gene occupy corresponding loci on a pair of homologous chromosomes.

Apparent starch amylose content. The amount of starch in the endosperm of milled rice that is amylose, provided in g/kg herein. Amylose content varies depending on the growth environment of the rice. It is an important grain characteristic used to describe cooking behavior.

Backcrossing. A process in which a breeder repeatedly crosses hybrid progeny back to a parental line. For example, a first generation (F1) hybrid may be crossed with one of the parental lines used to produce the F1 hybrids.

Breeding. The genetic manipulation of living organisms.

Cell. A cell is the basic structural unit of all organisms. As used herein, this term includes isolated cells, cells grown in tissue culture, and cells that comprise a plant or plant part.

Cultivar. Used interchangeably with "variety". Refers to plants with the characteristics of a particular genotype or combination of genotypes. Plants of a particular cultivar are distinguished from any other plant grouping by the expression of at least one characteristic.

Days to 50% heading. The average number of days from the emergence of a plant to the day when 50% of all panicles are exerted at least partially through the leaf sheath. A measure of maturity.

Embryo. The plant embryo is the part of a seed or bud that contains the earliest forms of the new plant's roots, stem and leaves.

Essentially all of the physiological and morphological characteristics. A plant having "essentially all the physiological and morphological characteristics" of the cultivar exhibits the characteristics of the cultivar with the exception of any characteristics derived from a converted gene or other trait being selected for.

F #. Denotes a filial generation, wherein # is the generation number. For example, F1 is the first filial generation.

Gene. Refers to a unit of inheritance corresponding to a distinct sequence of DNA that forms part of a chromosome. A gene may encode a polypeptide or a functional nucleic acid molecule.

Gene-converted. Describes a plant wherein essentially all of the desired morphological and physiological characteristics of a parental variety are maintained with the exception of a single trait that was transferred into the variety via backcrossing or genetic engineering.

Genotype. Refers to the genetic constitution of a cell or organism.

Grain yield. Measured in pounds per acre at 12.0% moisture content. The grain yield of rice is determined by the number of panicles per unit area, the number of fertile florets per panicle, and the grain weight per floret.

Haploid. A cell or organism having a single set of unpaired chromosomes.

Head rice. Kernels of milled rice in which greater than ¾ of the kernel is unbroken. Herbicide resistant. Describes a plant that is tolerant or resistant to an herbicide at a level that would normally kill or inhibit the growth of a normal or wild-type rice plant.

Hybrid. Refers to the progeny of genetically dissimilar plant parents or to stock produced by controlled cross-pollination (as opposed to a non-hybrid seed produced by natural pollination).

Lodging. The percentage of plant stems that are leaning or have fallen to the ground before harvest. Lodging is determined by visual scoring, in which crops are rated from 0% (all plants standing) to 100% (all plants lying flat on the soil surface). Lodged plants are difficult to harvest and reduce yield and grain quality. Lodging resistance is also called "straw strength".

Milling yield. The total amount of rice kernels (including both whole and broken kernels) recovered after milling (i.e., removal of hulls, bran, and germ). In contrast, head rice yield is the amount of whole kernels recovered after milling. Both values are expressed as a weight percentage of the original paddy or rough rice sample that was milled. Milling quality is often presented as a ratio of head rice yield to total rice yield. For example, for a sample of 100 grams of rough rice, a milling yield of 65:70 indicates that 65 grams of head rice and 70 grams of total milled rice were produced.

Pedigree. Refers to the lineage or genealogical descent of a plant.

Plant. As used herein, the term "plant" includes plant cells, plant protoplasts, and plant cell tissue cultures from which rice plants can be regenerated; plant calli, plant clumps and plant cells that are intact in plants; and parts of plants, such as embryos, pollen, ovules, flowers, glumes, panicles, leaves, stems, roots, root tips, anthers, and pistils.

Plant height. Measured in centimeters from the soil surface to the tip of the extended panicle at harvest.

Plant parts. Includes, without limitation, protoplasts, leaves, stems, roots, root tips, anthers, pistils, seed, grain, embryo, pollen, ovules, cotyledon, hypocotyl, pod, flower, shoot, tissue, petiole, cells, and meristematic cells.

Progeny. Includes an F1 rice plant produced from the cross of two rice plants, as well as plants produced from subsequent generational crosses (e.g., F2, F3, F4, F5, F6, F7, F8, F9, and F10) with the recurrent parental line.

Regeneration. Refers to the development of a plant from tissue culture.

Seeds. Includes seeds and plant propagules of all kinds including, but not limited to, true seeds, seed pieces, suckers, corms, bulbs, fruit, tubers, grains, cuttings, cut shoots, and the like. However, in preferred embodiments, it refers to true seeds.

Trait. Refers to an observable and/or measurable characteristic of an organism. For example, the present invention describes plants that have a trait that make them resistant to acetohydroxyacid synthase (AHAS) inhibiting herbicides.

Transgenic. Describes an organism or cell that contains genetic material that has been artificially introduced.

Wild-type. Used to refer to a gene that is common throughout a population and is, thus, arbitrarily designated the "normal" or "wild-type" form of the gene.

DETAILED DESCRIPTION OF THE INVENTION

The present invention provides a novel rice cultivar designated CLL16. The invention encompasses both the seeds of this cultivar and plants grown from these seeds. The invention further encompasses any rice plant having essentially all of the physiological and morphological characteristics rice cultivar CLL16.

As used herein, the term plant includes plant cells, plant protoplasts, plant cell tissue cultures from which rice plants can be regenerated, plant calli, plant clumps and plant cells that are intact in plants or parts of plants, such as embryos, pollen, ovules, flowers, glumes, panicles, leaves, stems, roots, root tips, anthers, pistils, and the like.

Development and Characterization of Rice Cultivar CLL16

CLL16 rice (Poaceae Oryzea *Oryza sativa* L.) is a very high yielding, short season, long-grain Clearfield® rice cultivar developed by the Arkansas Agricultural Experiment Station. CLL16 originated from the cross 'Wells'/CL161// 'Taggart'/3/'CL172' (cross no. 20123504), made at the Rice Research and Extension Center, Stuttgart, Ark., in 2012. Wells is a very stable high yielding cultivar, described in Moldenhauer et al., 2007. CL161, which was released by Louisiana State University Ag Center, contains the gene for resistance to imazethapyr and imazamox used in the Clearfield® system. Taggart is a very high yielding long-grain rice released by the Arkansas Agricultural Experiment Station in 2009 (Moldenhauer et al. 2009), and CL172 is a high yielding blast resistant Clearfield® long-grain released by the Arkansas Agricultural Experiment Station in 2014 released to BASF. CLL16 was developed using hybridization and a combination of modified pedigree and bulk breeding methods. This cultivar is adapted to growing in the Southern U.S. rice-growing region. The experimental designation for early evaluation of CLL16 was STG16IMI-13-016, starting with a bulk of F5 seed from the 2016 panicle row IMI-13-016. CLL16 was tested in the Arkansas Rice Performance Trials (ARPT) 2018-2019 (at Stuttgart, Ark.; Keiser, Ark.; Colt, Ark.; Rowher, Ark.; Jackson Co. Ark.; Cross Co, Ark.; and Clay Co Ark. and other DMP plots around the state of Arkansas) and in the Cooperative Uniform Regional Rice Nursery (URRN; at Stuttgart, Ark.; Crowley, La.; Beaumont, Tex.; Malden, Mo., and Stoneville, Miss.) during 2019 as entries STG16IMI-13-016 and CLL16, respectively (RU indicates Cooperative Uniform Regional Rice Nursery; 19 indicates the year it was entered was 2019; 01 indicates Stuttgart, Ark.; and 041 was the entry number).

CLL16 matures approximately 4 days earlier than 'Roy J' and is similar in maturity to 'CL153', CL172, and Wells. CLL16 is a standard statured cultivar, with an approximate 36-inch canopy height, which is similar to 'Diamond'. CLL16 has a strong straw strength, which is an indicator of lodging resistance. In 2018 ARPT, 2019 ARPT, and 2019 URRN it did not lodge. On a relative straw strength scale (0=very strong straw, 5=very weak straw based on percent lodging) CLL16, 'CL151', CL153, Diamond, Roy J and 'LaKast' rated 1.0, 1.6, 1.0, 1.1, 1.0, and 1.4, respectively in the 2018-2019 ARPT.

Rough rice grain yields of CLL16 ranked with Diamond in the 2018-2019 Arkansas Rice Performance Trials (ARPT). In nine ARPT tests (2018-2019), CLL16, CLL15, CL151, CL153, CLXL745, RT Gemini 214 CL, Diamond, and LaKast averaged yields of 206, 198, 194, 186, 202, 231, 205, and 190 bushels/acre, respectively. Data from the URRN conducted at Stuttgart, Ark., Crowley, La., and MO in 2019, showed that CLL16 average grain yield of 242 bushels/acre compared favorably with those of 'CL111', CL153, CLL15, 'CL163' and Diamond at 212, 225, 216, 204, and 241, bushels/acre, respectively. Milling yields (mg $g^{-1}$ whole kernel:mg $g^{-1}$ total milled rice) at 120 mg $g^{-1}$ moisture from the Riceland Foods Inc 2018 ARPT, averaged 630:690, 650:700, 660:690, 660:700, 650:700, 650:700, and 660:700, for CLL16, CL151, CL153, CLL15, Diamond, Roy J, and LaKast, respectively.

CLL16 has the blast resistance genes Pi-ta and Pi-kin, and like 'Katy' and 'Drew' is resistant to common rice blast (*Pyricularia grisea* (Cooke) Sacc) races IB-1, IB-17, IB-49, IC-17, and IE-1K, with summary ratings in greenhouse tests for 2019 of 0, 0, 0, 0, and 6, respectively, using the standard disease scale of 0=immune, 9=maximum disease susceptibility. CLL16 is susceptible to sheath blight (*Rhizoctonia solani* Kuhn), similar to CL153, Diamond and Wells. For comparison, some common varieties rate as follows: CL111 (VS), CL151 (S), CL153 (S), Diamond (S), Roy J (MS), Wells (S), and LaKast (MS) using the standard disease rating scale: R=resistant, MR=moderately resistant, MS=moderately susceptible, S=susceptible and VS=very susceptible to disease. CLL16 is rated MS to false smut (*Ustilaginoidea vixens* (Cooke) Takah), which compares favorably with Wells (S) and LaKast (S). Like 'CL152' and Roy J, CLL16 is rated S to bacterial panicle blight caused by *Burkholderia* species. CLL16 has a nitrogen fertilizer requirement of 135 lbs/acre.

Plants of CLL16 have erect culms, green erect leaves, and glabrous lemma, palea, and leaf blades. The lemma and palea are straw colored with red to purple apiculi, most of which fade to straw at maturity. CLL16 grain is of typical southern U.S. long-grain cooking quality. Kernels of CLL16 are desirably long and plump, with a grain size averaging 7.20 mm for the five locations of the 2018 ARPT compared to CLL15, CL151, and CL153 at 7.29, 6.90, and 7.27 mm/kernel, respectively. Individual milled kernel weights of CLL16, CL151, CL153, CLL15, and Diamond averaged 22.2, 20.6, 20.5, 21.9 and 21.7 mg/kernel, respectively, and has a chalk level of 1.72% compared to CL151, CL153, CLL15 and Diamond at 2.53%, 1.00%, 1.14%, and 1.67%, respectively, according to Riceland Foods Inc. Quality Laboratory from the 2018 ARPT samples.

The endosperm of CLL16 is nonglutinous, nonaromatic, and covered by a light brown pericarp. Rice quality parameters indicate that CLL16 has typical southern U.S. long-grain rice cooking quality characteristics as described by Webb et al. 1985. Based on the 2018 ARPT results from Riceland Foods Inc Quality Laboratory, CLL16 has an average apparent starch amylose content of 24.0 compared to CL153, CLL15, Diamond, Roy J and LaKast at 23.8, 23.4, 23.3, 24.0 and 23.9 g $kg^-$ and an intermediate gelatinization temperature of 69.6° C. compared to CL153, CLL15, Diamond, Roy J, and LaKast at 69.5° C., 68.6° C., 69.9° C., 69.3° C., and 68.9° C.

The breeder seed field of CLL16 was rogued several times throughout the season. The variants that may be found in the release include any combination of the following: taller, shorter, earlier, later, glabrous or pubescent plants, as well as intermediate or very-long slender grains. Other atypical plants may still be encountered in the cultivar. The total variants and/or off-types numbered less than 1 per 2000 plants.

Breeder seed of CLL16 will be maintained by the University of Arkansas Division of Agriculture Rice Research and Extension Center, P.O. 2900 Hwy 130 E., Stuttgart, Ark. 72160 and BASF.

The development timeline for CLL16 is shown in Table 1, below. The above-mentioned characteristics of rice cultivar CLL16 are based primarily on data collected in Stuttgart, Ark. and are summarized in Table 2. The results of the rice performance trials (ARPT 2018-2019, Clearfield test, and URRN 2019) are detailed in the Table 3-15. Tables 16-20 show grain yield data, and Tables 21-22 show nitrogen trial data.

TABLE 1

The Road to the development of CLL16

| Year | Program Stage |
| --- | --- |
| 2019 | ARPT (5 loc), Producer Rice Evaluation Program (PREP) (8 loc) and URRN (5 loc) and in the IMI ARPT which was which was treated with 3 times the rate of 16 oz Newpath/acre in a post application between 3 leaf and $2^{nd}$ tiller. BHR were grown and treated with 3 times the rate of 16 oz Newpath/acre in a post application between 3 leaf and $2^{nd}$ tiller at Stuttgart, AR. |
| 2018-2019 | Winter BHR (one Half of panicle) were grown in Puerto Rico with Horizon Ag and treated with Newpath herbicide to produce seed for future testing and seed increase. |
| 2018 | Arkansas Rice Performance Trials (ARPT) (5 loc) and Uniform Regional Rice Nursery (URRN) (5 loc) and in the IMI ARPT which was treated with 3 times the rate of 16 Newpath/acre in a post application between 3 leaf and $2^{nd}$ tiller. Panicles were selected from the IMI ARPT for breeder head row (BHR) and the seed from IMI ARPT was used for the seed source for the following year in the ARPT and URRN |
| 2017 | Summer: $F_5$ in IMI Stuttgart Initial Test Test (IMI SIT) Stuttgart, AR as STG16IMI-13-016 treated with 3 times the rate of 16 oz Newpath/acre in a post application between 3 leaf and $2^{nd}$ tiller. The plots which were used for future seed were rogued heavily checking for off-types |

TABLE 1-continued

The Road to the development of CLL16

| Year | Program Stage |
|---|---|
| 2016 | Summer: $F_4$ panicle row was grown in Stuttgart (IMI-13-016) treated with 3 times the rate of 16 oz Newpath/acre in a post application between 3 leaf and $2^{nd}$ tiller |
| 2015 | Summer: $F_3$ panicle row was grown in Stuttgart treated with 3 times the rate of 16 oz Newpath/acre in a post application between 3 leaf and $2^{nd}$ tiller. |
| 2014 | Summer: $F_2$ plants grown in field Lonoke, AR (LK-P10-2) treated with 3 times the rate of 16 oz product/acre in a post application of Newpath at the 3-4 leaf stage. |
| 2013 | Summer: $F_1$ plant grown in Transplants to produce F2 seed (Transplant #306) in Stuttgart, AR |
| 2012-2013 | Winter: $F_1$ plants are grown in the greenhouse in Stuttgart, AR |
| 2012 | Summer: Cross #20123504 (STG11IMI-07-211/CL172) Stuttgart, AR STG11IMI-07-211 has parentage Wells/CL161//Taggart |

TABLE 2

Cultivar description information

Plant:

Grain type: Long
Days to maturity (Seeding to 50% heading): approximately 86 (range 82-92 days)
Plant height: 112 cm (range 105-121 cm)
Plant color (at booting): Green
Plant Type:

Culm angle (degrees from perpendicular after flowering): Erect (less than 30°)
Flag leaf (after heading):

Pubescence: Glabrous
Leaf angle (after heading): Erect
Blade color (at heading): Green
Panicle:

Length: 26.0 cm (range 19 cm-32.5 cm)
Type: Intermediate
Axis: Droopy
Shattering (at maturity): Low (1-5%)
Grain (spikelet):

Awns (after full heading): Absent or tip awns at high fertility
Apiculus color: Brown (tawny)
Stigma color: White and light purple (1/3 light purple and 2/3 white, some variability)
Lemma and palea color (at maturity): Straw
Lemma and palea pubescence: Glabrous
Grain (seed):

Seed coat color: Light brown
Scent: Nonscented
Shape class (length/width ratio):

Paddy: Long (3.4:1 and more)
Brown: Long (3.1:1 and more)
Milled: Long (3.0:1 and more)
Size: 22.2 g/1000 seeds milled rice
Disease resistance:

Rice blast (*Pyricularia grisea* (Cooke) Sacc.): Moderately resistant
Sheath blight (*Rhizoctonia solani* Kuhn): Susceptible
False smut (*Ustilaginoidea virens* (Cooke) Takah.): Moderately susceptible
Bacterial panicle blight (*Burkholderia glumae* and *B. gladioli*): Susceptible
Narrow brown leaf spot (*Sphaerulina oryzina*): Resistant

TABLE 3

2018 Arkansas Rice Performance Trials (ARPT)
(Stuttgart, RREC; Keiser, NEREC; Clay County; Chicot County; Pinetree, PTRS)

| VARIETY | Avg. Grain Yield | Avg. Plant[b] Ht. (in.) | Avg. 50% Heading (days) | Avg. Straw Strength | Avg. Test Wt. (lbs.) | HR-TR[a] |
|---|---|---|---|---|---|---|
| CLL16 | 207 | 36 | 86 | 1 | 39.6 | 50:69 |
| CLL15 | 192 | 32 | 84 | 1 | 39.9 | 56:70 |
| CL151 | 185 | 33 | 80 | 1.2 | 39.9 | 54:70 |
| CL153 | 183 | 33 | 83 | 1 | 39.8 | 58:70 |
| RT CLXL745 | 190 | 37 | 77 | 1.6 | 39.7 | 52:70 |
| RT G214 CL | 235 | 39 | 82 | 1.4 | 40.1 | 53:69 |
| RT 7321 FP | 214 | 39 | 79 | 1.6 | 40.3 | 48.70 |
| Diamond | 206 | 36 | 83 | 1 | 39.9 | 52 69 |
| LaKast | 187 | 36 | 82 | 1 | 40.0 | 53:67 |
| Roy J | 189 | 38 | 90 | 1 | 39.4 | 54:69 |
| Wells | 184 | 37 | 85 | 1 | 39.9 | 48:71 |

[a]Milling figures are head rice: total milled rice
[b]Canopy height not to tip of panicle

TABLE 4

2019 Arkansas Rice Performance Trials (ARPT)
(Stuttgart, RREC; Keiser, NEREC; Clay County; Chicot County; Pinetree, PTRS)

| VARIETY | Avg. Grain Yield | Avg. Plant[b] Ht. (in.) | Avg. 50% Heading (days) | Avg. Straw Strength | Avg. Test Wt. (lbs.) | HR-TR[a] |
|---|---|---|---|---|---|---|
| CLL16 | 205 | 36 | 87 | 0 | 39.7 | 55:68 |
| CLL15 | 206 | 31 | 84 | 0 | 40.4 | 59:69 |
| CL151 | 205 | 34 | 82 | 0 | 40.2 | 62:71 |
| CL153 | 189 | 32 | 85 | 0 | 40.0 | 62:71 |
| RT CLXL745 | 217 | 36 | 79 | .6 | 41.6 | 57:71 |
| RT G214 CL | 225 | 37 | 83 | 0 | 40.5 | 57:70 |
| RT 7321 FP | 237 | 38 | 79 | 0 | 41.2 | 55:71 |
| Diamond | 206 | 35 | 85 | 0 | 40.5 | 58:70 |
| LaKast | 187 | 34 | 82 | 0 | 41.1 | 58:70 |

[a]Milling figures are head rice: total milled rice only RREC, NEREC, Clay Co. and PTRS
[b]Canopy height not to tip of panicle

TABLE 5

2018-2019 Arkansas Rice Performance Trials (ARPT)
(Stuttgart, RREC; Keiser, NEREC; Clay County;
Chicot County; Pinetree, PTRS)

| VARIETY* | YIELD (BU/AC) | HEIGHT (IN.) | MATURITY (50% HD) | MILLING HR:TOT |
|---|---|---|---|---|
| CLL16 | 206 | 36 | 87 | 53:69 |
| CLL15 | 198 | 32 | 84 | 57:70 |
| CL151 | 194 | 34 | 82 | 58:70 |
| CL153 | 186 | 33 | 84 | 60:71 |
| RT CL 745 | 202 | 37 | 78 | 55:70 |
| RT G214 CL | 231 | 38 | 83 | 55:70 |
| RT 7321 FP | 224 | 39 | 79 | 52:70 |
| Diamond | 205 | 36 | 84 | 55:69 |
| LaKast | 190 | 35 | 82 | 56:69 |

Mean of the 2018 and 2019 ARPT Trials on pages 8 and 9. CLAY, DESHA, NEREC, PTRS, and RREC in 2018 and CLAY, NEREC, PTRS, and RREC in 2019

TABLE 6

2018 Arkansas Rice Performance Trials (ARPT): Means by location

| | GRAIN YIELD (BU/AC)[b] | | | | | | HEAD RICE (%) - TOTAL RICE (%) | | | | | |
|---|---|---|---|---|---|---|---|---|---|---|---|---|
| VARIETY | CLAY | CHICOT | NEREC | PTRS | RREC | MEAN | CLAY | CHICOT | NEREC | PTRS | RREC | MEAN |
| CLXAR19[a] | 224 | 207 | 189 | 214 | 198 | 207 | 43:71 | 59:71 | 44:67 | 51:69 | 55:67 | 50:70 |
| CLL15 | 212 | 194 | 157 | 194 | 201 | 192 | 51:72 | 61:71 | 50:67 | 56:70 | 62:71 | 56:70 |
| CL151 | 198 | 184 | 157 | 196 | 190 | 185 | 46:71 | 61:71 | 44:67 | 55:69 | 63:70 | 54:70 |
| CL153 | 198 | 188 | 160 | 180 | 189 | 186 | 53:71 | 62:71 | 52:68 | 58:70 | 63:70 | 58:70 |
| RT CL745 | 214 | 190 | 116 | 209 | 221 | 190 | 41:72 | 60:72 | 49:69 | 53:69 | 60:69 | 52:70 |
| RT G214 CL | 247 | 232 | 226 | 240 | 231 | 235 | 41:72 | 59:71 | 51:66 | 54:69 | 59:69 | 53:69 |
| RT 7321 FP | 245 | 218 | 170 | 223 | 217 | 214 | 33:72 | 57:71 | 40:68 | 49:70 | 60:69 | 48:70 |
| Diamond | 228 | 213 | 189 | 195 | 204 | 206 | 48:72 | 57:70 | 50:68 | 51:69 | 57:68 | 52:69 |
| LaKast | 213 | 181 | 161 | 190 | 191 | 187 | 54:72 | 58:71 | 42:54 | 52:70 | 58:70 | 53:67 |
| RoyJ | 204 | 178 | 178 | 190 | 193 | 189 | 50:72 | 58:71 | 55:69 | 54:69 | 52:66 | 54:69 |
| Wells | 211 | 185 | 164 | 172 | 189 | 184 | 38:73 | 58:71 | 38:69 | 47:70 | 57:70 | 48:71 |

[a]experimental line STG6IMI-13-016
[b]Yield trials in 2018, Clay County Farmers Field (CLAY); Chicot County Whitaker Farm,Field (CHICOT); Northeast Research and Extension Center, (NEREC), Keiser, AR, Pine Tree Research Station, (PTRS), Colt, AR; and Rice Research and Extension Center, (RREC).

TABLE 7

2019 Arkansas Rice Performance Trials (ARPT): Means by location

| | GRAIN YIELD (BU/AC)[a] | | | | | HEAD RICE (%) - TOTAL RICE (%) | | | | |
|---|---|---|---|---|---|---|---|---|---|---|
| VARIETY | CLAY | NEREC | PTRS | RREC | MEAN | CLAY | NEREC | PTRS | RREC | MEAN |
| CLL16[b] | 207 | 187 | 193 | 233 | 205 | 60:70 | 55:66 | 54:69 | 51:66 | 55:68 |
| CLL15 | 224 | 200 | 185 | 214 | 206 | 64:71 | 63:69 | 48:69 | 61:69 | 59:69 |
| CL151 | 221 | 208 | 187 | 206 | 205 | 67:72 | 64:70 | 53:70 | 63:70 | 62:71 |
| CL153 | 209 | 192 | 168 | 188 | 189 | 68:73 | 63:69 | 54:71 | 63:70 | 62:71 |
| RT CL745 | 236 | 214 | 192 | 225 | 217 | 63:73 | 64:71 | 46:70 | 57:70 | 57:71 |
| RT G214 CL | 239 | 217 | 214 | 251 | 230 | 61:72 | 60:68 | 47:69 | 58:69 | 57:70 |
| RT 7321 FP | 256 | 237 | 206 | 248 | 237 | 61:73 | 62:71 | 42:70 | 55:70 | 55:71 |
| Diamond | 226 | 193 | 179 | 219 | 204 | 63:72 | 62:69 | 52:70 | 55:68 | 58:70 |
| LaKast | 203 | 202 | 161 | 213 | 195 | 64:72 | 60:69 | 49:70 | 57:70 | 58:70 |

[a]Yield trials in 2019, Clay County Farmer Field, (CLAY), Corning, AR; Northeast Research and Extension Center, (NEREC), Keiser, AR; Pine Tree Research Station, (PTRS), Colt, AR; and Rice Research and Extension Center, (RREC),
[b]CLL16 is CLXAR19

TABLE 8

2018-2019 Arkansas Rice Performance Trials (ARPT): Means by location

| | GRAIN YIELD (BU/AC) | | | | | HEAD RICE (%) - TOTAL RICE (%) | | | | |
|---|---|---|---|---|---|---|---|---|---|---|
| VARIETY | CLAY | NEREC | PTRS | RREC | MEAN | CLAY | NEREC | PTRS | RREC | MEAN |
| CLL16 | 216 | 188 | 205 | 214 | 206 | 51:71 | 50:67 | 52:69 | 53:67 | 52:68 |
| CLL15 | 217 | 176 | 190 | 207 | 198 | 57:72 | 57:68 | 52:69 | 61:70 | 57:70 |
| CL151 | 208 | 180 | 192 | 197 | 194 | 56:72 | 54:68 | 54:70 | 63:70 | 57:70 |
| CL153 | 203 | 174 | 175 | 189 | 186 | 60:72 | 57:68 | 56:70 | 63:70 | 59:70 |
| RT CL745 | 224 | 160 | 201 | 223 | 202 | 52:73 | 56:70 | 50:70 | 58:70 | 54:70 |

TABLE 8-continued 2018-2019 Arkansas Rice Performance Trials (ARPT): Means by location

| | GRAIN YIELD (BU/AC) | | | | | HEAD RICE (%) - TOTAL RICE (%) | | | | |
|---|---|---|---|---|---|---|---|---|---|---|
| VARIETY | CLAY | NEREC | PTRS | RREC | MEAN | CLAY | NEREC | PTRS | RREC | MEAN |
| RT G214 CL | 243 | 222 | 228 | 240 | 233 | 51:72 | 56:67 | 50:69 | 59:69 | 54:69 |
| RT 7321 FP | 250 | 200 | 215 | 242 | 224 | 47:73 | 51:69 | 45:70 | 57:69 | 50:70 |
| Diamond | 227 | 191 | 188 | 211 | 205 | 55:72 | 56:69 | 51:70 | 56:68 | 55:69 |
| LaKast | 207 | 181 | 167 | 200 | 189 | 59:72 | 51:61 | 51:70 | 58:70 | 55:68 |

[a]Yield trials in 2019, Clay County Farmer Field, (CLAY), Corning, AR; Northeast Research and Extension Center, (NEREC), Keiser, AR; Pine Tree Research Station, (PTRS), Colt, AR; and Rice Research and Extension Center, (RREC),
[b]CLL161 is CLXAR19

TABLE 9

2018 Clearfield Test (performed in Stuttgart, AR; 2 replications)

| VARIETY | YIELD BU/ACRE | DAYS TO 50% HEAD | HEIGHT IN CM | CUP WEIGHT | %HEAD: %TOTAL |
|---|---|---|---|---|---|
| CLL16 | 186 | 85 | 116 | 41.2 | 56:67 |
| CL151 | 190 | 77 | 100 | 38.4 | 60:68 |
| CL153 | 146 | 83 | 108 | 37.7 | 60:67 |
| RT GEM214 CL | 229 | 79 | 121 | 37.4 | 59:67 |

TABLE 10

2019 Clearfield Test (performed in Stuttgart, AR; 2 replications)

| VARIETY | YIELD BU/ACRE | DAYS TO 505 HEAD | HEIGHT (CM) | CUP WEIGHT | %HEAD: %TOTAL |
|---|---|---|---|---|---|
| CLL16 | 189 | 86 | 104 | 41.8 | 58:68 |
| CL151 | 176 | 83 | 99 | 40.0 | 61:70 |
| CL153 | 180 | 83 | 96 | 41.6 | 61:72 |
| RT Gem214 CL | 220 | 81 | 116 | 37.2 | 56:69 |

TABLE 11

2019 Uniform Regional Rice Nursery (URRN) Yield and Agronomic Data (from Stuttgart, AR; and Crowley, LA)

| | YIELD IN LBS | | | | | DAYS TO 50% HEAD | | | | PLANT HEIGHT (cm) | | | | % LODGING[a] | | | |
|---|---|---|---|---|---|---|---|---|---|---|---|---|---|---|---|---|---|
| VARIETY | AR | LA | MO | AVG | Ave Bu/a | AR | LA | MO | AVG | AR | LA | MO | AVG | AR | LA | MO | AVG |
| CLL16 | 10049 | 9602 | 13085 | 10912 | 242 | 92 | 88 | 104 | 95 | 110 | 109 | 108 | 109 | 0 | 0 | | |
| CL111 | 8787 | 10480 | 9413 | 9560 | 212 | 85 | 80 | 108 | 91 | 106 | 102 | 97 | 102 | 0 | 0 | | |
| CL153 | 10016 | 10579 | 9728 | 10108 | 225 | 90 | 83 | 112 | 95 | 106 | 105 | 97 | 103 | 0 | 0 | | |
| CLL15 | 9402 | 9564 | 10156 | 9707 | 216 | 86 | 83 | 98 | 89 | 96 | 99 | 97 | 97 | 0 | 0 | | |
| CL163 | 9899 | 8453 | 9241 | 9198 | 204 | 90 | 88 | 105 | 94 | 108 | 108 | 106 | 107 | 0 | 0 | | |
| Diamond | 11404 | 9124 | 12074 | 10867 | 241 | 89 | 85 | 98 | 91 | 111 | 109 | 104 | 108 | 0 | 0 | | |
| Roy J | 9105 | 8502 | 12375 | 9994 | 222 | 95 | 89 | 106 | 97 | 115 | 111 | 117 | 114 | 0 | 0 | | |

TABLE 12

2018 Riceland Laboratory Arkansas Rice Performance Trials (ARPT) quality data

| | | | Milling Data | | | | | | | | Kernel |
|---|---|---|---|---|---|---|---|---|---|---|---|
| Loc | Cultivar | Rep | Head Yield | Total Yeild | Hull Yield | Bran Yield | Chalk | Length | Width | Thickness | L:W Ratio | Weight |
| Clay | CLXAR19 | 1 | 60.9 | 71.4 | 18.2 | 10.4 | 1.38 | 7.32 | 2.24 | 1.76 | 3.27 | 22.4 |
| Clay | CLXAR19 | 3 | 63.4 | 72.2 | 16.4 | 11.4 | 0.92 | 6.83 | 2.21 | 1.73 | 3.09 | 20.7 |
| NEREC | CLXAR19 | 1 | 55.9 | 66.2 | 16.9 | 17.0 | 1.86 | 7.26 | 2.25 | 1.76 | 3.23 | 23.4 |
| NEREC | CLXAR19 | 3 | 63.5 | 68.0 | 19.1 | 12.9 | 1.77 | 7.22 | 2.29 | 1.75 | 3.15 | 22.9 |
| Chicot | CLXAR19 | 1 | 67.8 | 70.6 | 15.5 | 13.9 | 1.01 | 7.42 | 2.18 | 1.78 | 3.40 | 23.1 |
| Chicot | CLXAR19 | 3 | 65.7 | 69.8 | 16.6 | 13.6 | 2.08 | 7.15 | 2.16 | 1.68 | 3.31 | 21.8 |
| PTRS | CLXAR19 | 1 | 62.7 | 69.0 | 17.0 | 14.1 | 2.22 | 7.18 | 2.14 | 1.73 | 3.36 | 21.5 |
| PTRS | CLXAR19 | 3 | 65.9 | 70.1 | 17.4 | 12.5 | 1.82 | 7.09 | 2.25 | 1.75 | 3.15 | 21.9 |
| RREC | CLXAR19 | 1 | 62.6 | 65.1 | 16.1 | 18.8 | 2.19 | 7.42 | 2.21 | 1.73 | 3.36 | 22.8 |
| RREC | CLXAR19 | 3 | 61.4 | 66.2 | 16.3 | 17.4 | 1.92 | 7.08 | 2.15 | 1.72 | 3.29 | 21.5 |
| | | Ave | 63.0 | 68.9 | 16.9 | 14.2 | 1.72 | 7.20 | 2.21 | 1.74 | 3.26 | 22.2 |
| | | Min | 55.9 | 65.1 | 15.5 | 10.4 | 0.92 | 6.83 | 2.14 | 1.68 | 3.09 | 20.7 |
| | | Max | 67.8 | 72.2 | 19.1 | 18.8 | 2.22 | 7.42 | 2.29 | 1.78 | 3.40 | 23.4 |

TABLE 13

2018 Riceland Laboratory Arkansas Rice Performance Trials (ARPT) quality data CONTINUED

| Loc | Cultivar | Rep | Gel Temp | Amylose | RVA Peak | Trough | Breakdown | Final | Setback | Satake Whiteness | Milling Degree |
|---|---|---|---|---|---|---|---|---|---|---|---|
| Clay | CLXAR19 | 1 | 68.94 | 23.95 | 288 | 162 | 126 | 315 | 27 | 40.3 | 91 |
| Clay | CLXAR19 | 3 | 68.13 | 27.21 | 270 | 160 | 110 | 306 | 36 | 43.2 | 107 |
| NEREC | CLXAR19 | 1 | 68.83 | 21.82 | 270 | 156 | 114 | 302 | 32 | 41.0 | 94 |
| NEREC | CLXAR19 | 3 | 69.28 | 23.18 | 272 | 158 | 113 | 303 | 31 | 41.8 | 101 |
| Chicot | CLXAR19 | 1 | 70.30 | 22.90 | 305 | 179 | 126 | 337 | 32 | 38.1 | 81 |
| Chicot | CLXAR19 | 3 | 70.35 | 22.36 | 292 | 175 | 117 | 327 | 35 | 39.3 | 87 |
| PTRS | CLXAR19 | 1 | 69.74 | 23.37 | 305 | 176 | 129 | 330 | 25 | 42.0 | 100 |
| PTRS | CLXAR19 | 3 | 70.50 | 24.58 | 299 | 175 | 124 | 328 | 29 | 37.0 | 77 |
| RREC | CLXAR19 | 1 | 69.68 | 27.39 | 306 | 183 | 123 | 333 | 27 | 43.8 | 111 |
| RREC | CLXAR19 | 3 | 70.01 | 23.28 | 299 | 177 | 122 | 328 | 29 | 37.7 | 82 |
| | | Ave | 69.58 | 24.00 | 291 | 170 | 120 | 321 | 30 | 40.4 | 93 |
| | | Min | 68.13 | 21.82 | 270 | 156 | 110 | 302 | 25 | 37.0 | 77 |
| | | Max | 70.50 | 27.39 | 306 | 183 | 129 | 337 | 36 | 43.8 | 111 |

TABLE 14

2018 Riceland Laboratory Arkansas Rice Performance Trials (ARPT) means

| Cultivar | AVE | Milling Data | | | | Satake | | Moisture (%) | Chalk (%) | Length (mm) | Width (mm) | Thickness (mm) |
| | | Head Yield | Total Yield | Hull Yield | Bran Yield | Whiteness | Milling Degree | | | | | |
|---|---|---|---|---|---|---|---|---|---|---|---|---|
| CLL16 | Ave | 63.0 | 68.9 | 16.9 | 14.2 | 40.4 | 93 | 8.71 | 1.72 | 7.20 | 2.21 | 1.74 |
| CL151 | Ave | 64.7 | 69.7 | 18.3 | 12.0 | 37.9 | 80 | 8.43 | 2.53 | 6.90 | 2.23 | 1.70 |
| CL153 | Ave | 66.0 | 69.4 | 16.9 | 13.7 | 41.8 | 99 | 8.76 | 1.00 | 7.27 | 2.10 | 1.69 |
| CLL15 | Ave | 66.3 | 69.9 | 17.1 | 13.0 | 44.1 | 109 | 8.92 | 1.14 | 7.29 | 2.19 | 1.71 |
| Diamond | Ave | 65.1 | 69.9 | 18.0 | 12.1 | 38.9 | 86 | 8.59 | 1.67 | 7.26 | 2.11 | 1.74 |
| Roy J | Ave | 64.6 | 69.5 | 18.2 | 12.3 | 38.3 | 84 | 8.92 | 1.06 | 7.25 | 2.07 | 1.74 |
| LaKast | Ave | 66.1 | 70.3 | 17.6 | 12.1 | 42.1 | 101 | 8.61 | 1.42 | 7.52 | 2.10 | 1.72 |

TABLE 15

2018 Riceland Laboratory Arkansas Rice Performance Trials (ARPT) means CONTINUED

| Cultivar | AVE | L:W Ratio | Weight (mg) | Gel Temp (° C.) | Amylose (%) | RVA (rvu) Peak | Trough | Breakdown | Final | Setback |
|---|---|---|---|---|---|---|---|---|---|---|
| CLL16 | Ave | 3.26 | 22.2 | 69.58 | 24.00 | 291 | 170 | 120 | 321 | 30 |
| CL151 | Ave | 3.10 | 20.6 | 70.84 | 23.20 | 288 | 156 | 132 | 306 | 18 |
| CL153 | Ave | 3.46 | 20.5 | 69.51 | 23.83 | 290 | 153 | 137 | 308 | 19 |
| CLL15 | Ave | 3.33 | 21.9 | 68.60 | 23.41 | 288 | 162 | 126 | 309 | 22 |
| Diamond | Ave | 3.45 | 21.7 | 69.94 | 23.15 | 286 | 150 | 137 | 299 | 13 |
| Roy J | Ave | 3.51 | 20.8 | 69.28 | 23.99 | 281 | 145 | 135 | 293 | 12 |
| LaKast | Ave | 3.58 | 2.21 | 68.92 | 23.86 | 291 | 162 | 130 | 316 | 24 |

TABLE 16

2019 DD50* Data: Rice Research & Extension Center

| Cultivar | Grain Yields | | | | | |
| | 21 Mar. | 3 Apr. | 16 Apr. | 29 Apr. | 17 May | 4 Jun. | Average |
|---|---|---|---|---|---|---|---|
| Diamond | 233 | 235 | 223 | 220 | 205 | 201 | 219 |
| CLARX19 | 244 | 255 | 231 | 226 | 211 | 194 | 227 |
| CLL15 | 222 | 222 | 220 | 193 | 173 | 177 | 201 |
| CLM04 | 230 | 209 | 226 | 208 | 197 | 180 | 208 |
| CL153 | 226 | 224 | 202 | 188 | 177 | 176 | 199 |
| 'CL272' | 232 | 220 | 236 | 192 | 192 | 188 | 210 |
| CLXL745 | 203 | 231 | 226 | 224 | 224 | 201 | 218 |

TABLE 16-continued

2019 DD50* Data: Rice Research & Extension Center

| Cultivar | Grain Yields | | | | | |
| | 21 Mar. | 3 Apr. | 16 Apr. | 29 Apr. | 17 May | 4 Jun. | Average |
|---|---|---|---|---|---|---|---|
| G214CL | 250 | 260 | 271 | 243 | 248 | 203 | 246 |
| Mean | 234 | 231 | 233 | 221 | 209 | 197 | 221 |

*The DD50 program was developed in the 1970's to help rice farmers accurately time mid-season nitrogen applications. The DD50 is a modification of the growing degree-day concept, which uses temperature data to predict rice development.

TABLE 17

2019 DD50 Data: Pine Tree Research Station

| Cultivar | 2 Apr. | 24 Apr. | 8 May | 28 May | 12 Jun. | Average |
|---|---|---|---|---|---|---|
| Diamond | 159 | 236 | 199 | 186 | | 195 |
| CLARX19 | 169 | 230 | 204 | 183 | | 196 |
| CLL15 | 163 | 237 | 202 | 167 | | 192 |
| CLM04 | 167 | 208 | 210 | 185 | | 192 |
| CL153 | 134 | 178 | 164 | 143 | | 155 |
| CL272 | 123 | 207 | 183 | 138 | | 163 |
| CLXL745 | 147 | 231 | 207 | 158 | | 186 |
| G214CL | 171 | 255 | 214 | 200 | | 210 |
| Mean | 160 | 228 | 199 | 173 | | 190 |

TABLE 18

Preliminary Data Summary: 2019 Planting Date Study at RREC, Stuttgart

| | Grain Yields | | | | | | |
|---|---|---|---|---|---|---|---|
| Cultivar | 21 Mar. | 3 Apr. | 16 Apr. | 29 Apr. | 17 May | 4 Jun. | Average |
| Diamond | 233 | 235 | 223 | 220 | 205 | 201 | 219 |
| 'ARoma17' | 201 | 186 | 178 | 171 | 151 | 157 | 174 |
| ARX7-1087 | 222 | 221 | 219 | 211 | 205 | 195 | 212 |
| CLL16 | 244 | 255 | 231 | 226 | 211 | 194 | 227 |
| CLL15 | 222 | 222 | 220 | 193 | 173 | 177 | 201 |
| CLM04 | 230 | 209 | 226 | 208 | 197 | 180 | 208 |
| 'PVL01' | 199 | 194 | 187 | 179 | 164 | 161 | 181 |
| RT 3201 | 219 | 222 | 225 | 212 | 198 | 180 | 209 |
| RT 7301 | 269 | 258 | 258 | 261 | 222 | 221 | 248 |
| 7321FP | 237 | 239 | 256 | 257 | 240 | 227 | 243 |
| RT 7501 | 261 | 263 | 277 | 265 | 250 | 224 | 257 |
| 7521FP | 230 | 240 | 252 | 232 | 229 | 206 | 232 |
| CL153 | 226 | 224 | 202 | 188 | 177 | 176 | 199 |
| CL272 | 232 | 220 | 236 | 192 | 192 | 188 | 210 |
| 'Jupiter' | 248 | 229 | 238 | 227 | 210 | 198 | 225 |
| 'Titan' | 239 | 226 | 230 | 217 | 208 | 207 | 221 |
| CLXL745 | 203 | 231 | 226 | 224 | 224 | 201 | 218 |
| G214CL | 250 | 260 | 271 | 243 | 248 | 203 | 246 |
| 'XP753' | 259 | 251 | 271 | 264 | 252 | 233 | 255 |
| Mean | 234 | 231 | 233 | 221 | 209 | 197 | 221 |

TABLE 19

Preliminary Data Summary: 2019 Planting Date Study at PTRS, Colt

| Cultivar | 2 Apr. | 24 Apr. | 8 May | 28 May | 12 Jun. | Average |
|---|---|---|---|---|---|---|
| Diamond | 159 | 236 | 199 | 186 | 165 | 189 |
| ARoma17 | 155 | 197 | 166 | 157 | 148 | 164 |
| ARX7-1087 | 160 | 215 | 185 | 165 | 144 | 174 |
| CLL16 | 169 | 230 | 204 | 183 | 157 | 188 |
| CLL15 | 163 | 237 | 202 | 167 | 162 | 186 |
| CLM04 | 167 | 208 | 210 | 185 | 163 | 186 |
| PVL01 | 149 | 180 | 165 | 147 | 126 | 153 |
| RT 3201 | 171 | 208 | 192 | 164 | 164 | 180 |
| RT 7301 | 161 | 259 | 210 | 174 | 158 | 192 |
| 7321FP | 157 | 266 | 215 | 173 | 169 | 196 |
| RT 7501 | 177 | 234 | 197 | 178 | 193 | 196 |
| 7521FP | 175 | 245 | 227 | 215 | 196 | 212 |
| CL153 | 134 | 178 | 164 | 143 | 125 | 149 |
| CL272 | 123 | 207 | 183 | 138 | 131 | 157 |
| Jupiter | 159 | 231 | 210 | 188 | 182 | 194 |
| Titan | 137 | 232 | 189 | 183 | 149 | 178 |
| CLXL745 | 147 | 231 | 207 | 158 | 156 | 180 |
| G214CL | 171 | 255 | 214 | 200 | 191 | 206 |
| XP753 | 175 | 266 | 218 | 182 | 185 | 205 |
| Mean | 160 | 228 | 199 | 173 | 161 | 184 |

TABLE 20

Prep Test Data: Grain Yield

| Cultivar | Grain Type | Greene | Lee | Lonoke | Poinsett | Prairie | Woodruff | AVG Grain Yield | Rank |
|---|---|---|---|---|---|---|---|---|---|
| Diamond | L | 178 | 209 | | 221 | 181 | 262 | 210 | 10 |
| CLM04 | M | 188 | 208 | | 170 | 176 | 197 | 188 | 18 |
| CL272 | M | 163 | 232 | | 185 | 163 | 221 | 193 | 17 |
| CL151 | L | 180 | 231 | | 195 | 153 | 219 | 196 | 15 |
| CL153 | L | 160 | 211 | | 186 | 168 | 205 | 186 | 19 |
| CLL15 | L | 192 | 238 | | 205 | 173 | 201 | 202 | 13 |
| CLXAR19 | L | 197 | 246 | | 224 | 212 | 245 | 225 | 5 |
| RTCLXL745 | L | 197 | 210 | | 207 | 196 | 229 | 208 | 11 |
| RTGEM214 | L | 211 | 250 | | 233 | 219 | 264 | 235 | 2 |
| Mean | | 185 | 226 | | 203 | 182 | 227 | 205 | |

TABLE 21

CLL16 - 2019 Variety by Nitrogen Trials: Pertinent agronomic information for the Northeast Research and Extension Center (NEREC), Pine Tree Research Station (PTRS), and the Rice Research and Extension Center (RREC) during 2015.

| PRACTICES | NEREC | PTRS** | RREC |
|---|---|---|---|
| Pre-plant Fertilizer | | | 0-60-90 + 10 lbs Zn as ZnSO4 |
| Planting Dates | 5/4 | 6/5 | 5/1 |
| Herbicide Spray Dates and | 5/6 40 oz/acre Facet L + 1.3 pt/acre Command + | 6/5 1.0 pt/acre Command + 0.75 | 5/1 20 oz/acre Obey |

TABLE 21-continued

CLL16 - 2019 Variety by Nitrogen Trials: Pertinent agronomic information for the
Northeast Research and Extension Center (NEREC), Pine Tree Research Station (PTRS),
and the Rice Research and Extension Center (RREC) during 2015.

| PRACTICES | NEREC | PTRS** | RREC |
|---|---|---|---|
| Spray Procedures | 0.75 oz/acre Permit Plus + 32 oz/acre RoundUp | oz/acre Permit Plus | |
| Flush Dates | | | |
| Emergence Dates | 5/20 | 6/11 | 5/10 |
| Herbicide Spray Dates and Spray Procedures | 6/11 4 qt/acre Stam + 1 pt/acre Grandstand | 6/16 3 qt/acre Riceshot + 32 oz/acre Facet L | 6/1 2 qt Prowl + 0.75 oz/acre Permit Plus |
| Herbicide Spray Dates and Spray Procedures | | 6/23 32 oz/acre Facet L + 1 pt/acre Bolero | |
| Herbicide Spray Dates and Spray Procedures | | | |
| Preflood N Dates | 6/18 | 6/24 | 6/3 |
| Flood Dates | 6/19 | 6/25 | 6/4 |
| Drain Dates | 9/9 | 10/1 | 8/28 |
| Harvest Dates | 9/23 | 10/14 | 9/2 |

**Zinc EDTA applied (7/10)

TABLE 22

Influence of nitrogen (N) fertilizer rate on the grain yield of
CLL16 rice at three locations during 2019.

| N fertilizer rate --- (lbs N/A) --- | PTRS* | RREC |
|---|---|---|
| 0 | 90 | 119 |
| 60 | 142 | 171 |
| 90 | 152 | 184 |
| 120 | 175 | 203 |
| 150 | 182 | 215 |
| 180 | 179 | 208 |

*PTRS = Pine Tree Research Station, Colt, AR; RREC = Rice Research and Extension Center, Stuttgart, AR.
$^b$LSD = least significant difference, C.V. = coefficient of variation.

Disease Evaluations of CLL16

Funding to improve and utilize varietal resistance for the control of rice diseases in Arkansas comes almost entirely from grower check-off monies administered by the Rice Research and Promotion Board. These funds are used to monitor and identify diseases in order to establish resource allocation priorities, conduct preliminary research needed to identify and improve genetic resistance sources, support the greenhouse and field disease evaluations on experiment stations and in grower fields, and maintain qualified support staff necessary to incorporate quality disease resistance in new cultivars released for use by Arkansas rice producers.

Varietal resistance is the most efficient and reliable means of controlling rice diseases. Conservation and improvement of disease resistance is a continuous endeavor basic to varietal development. Incorporation of existing and new resistance sources is a complex process limited by several variables. The rice disease research program routinely evaluates breeding program entries to provide disease data required for superior variety development. Our objectives are to increase varietal disease resistance and to define disease liabilities of new varieties released for rice production in Arkansas.

Most rice diseases are rated visually on a 0-9 scale to estimate degree of severity. Numerical data are often converted to this scale. A rating of zero indicates no disease. A rating of one to three indicates resistance where little loss may occur. Conversely, a nine rating indicates maximum disease, which typically results in a susceptible reaction and hence, substantial yield loss in severe disease epidemic situations. Depending upon the disease in question, a disease rating of four to six is usually indicative of acceptable disease resistance under conditions slightly favoring the pathogen. Numerical ratings are sometimes converted to letter symbols where 0-3=R (resistant), 3-4=MR (moderately resistant), 5-6=MS (moderately susceptible) 7=S (susceptible) and 8-9 VS (very susceptible). Exceptions to established ratings may occur unexpectedly as disease situations change.

These data come from several sources. Advanced and promising breeding lines are evaluated by researchers in Arkansas and other states. It is not unusual for ratings to vary across locations and years due to environmental differences and research procedures, whereas ratings within a source traditionally have been consistent.

Greenhouse blast tests are the primary means of screening large number of entries for varietal reaction to the common blast races occurring in the production areas. Although results are quite variable and testing conditions tend to overwhelm any field resistance that may be present in the rice, this test provides an accurate definition of the fungus by variety genetics. Blast field nurseries utilize natural and lab produced inoculum to better define their resistance under field conditions. Field nurseries are established and artificially inoculated to provide a uniform disease pressure for evaluations under field conditions. Due to several variables in the field, new techniques are currently being developed and evaluated to better estimate cultivar field resistance to blast.

Nurseries are also established in growers' fields across the state to evaluate disease reactions in production fields using producers' practices. Over time, these nurseries document variety performance under different disease conditions in Arkansas production fields.

Below, Tables 23-24 show disease evaluation data, collected by Dr. Wamishe.

Table 23. Summary of available leaf blast rating data from CLL16 plants inoculated with the indicated race using standard greenhouse techniques, 2019. Note: CLL16 has the genes for blast resistance Pi-ta gene and Pi-km.

| | IB-1 | IB-17 | IB-49 | IC-17 | IE-1K | IE-1 |
|---|---|---|---|---|---|---|
| Greenhouse leaf blast ratings | 0 | 0 | 0 | 0 | 6 | 0 |

TABLE 24

Rice variety reactions[1] to diseases (2018-2019)

| Cultivar | Sheath Blight | Blast | Straighthead | Bacterial Panicle Blight | Narrow Brown Leaf Spot | Stem Rot | Kernel Smut | False Smut | Lodging | Black Sheath Rot |
|---|---|---|---|---|---|---|---|---|---|---|
| CLXAR19 | S | MS |  | S | R |  |  | MS |  |  |
| CL111 | VS | MS | S | VS | S | VS | S | S | MS | S |
| CL151 | S | VS | VS | VS | S | VS | S | S | S | S |
| CL153 | S | MS |  | MS | S |  | S | S | MR |  |
| CLL15 Diamond | S | S |  | MS |  | S | S | VS | MS |  |
| LaKast | MS | S | MS | MS | MS | S | S | S | MS | MS |
| Roy J | MS | S | S | S | R | S | VS | S | MR | MS |
| RiceTec CL XL729 | MS | R | MS | MR | R | S | MS | S | S | S |
| RiceTec CL XL745 | S | R | R | MR | MS | S | MS | S | S | S |
| RiceTec XL753 | MS | R | MS | MR | R |  | MS | S | MS | S |
| RiceTec XP760 | MS | MR |  | MR | R |  | MS | VS | S |  |
| Wells | S | S | S | S | S | VS | S | S | MS | MS |

1Reaction: R = Resistant; MR = Moderately Resistant; MS = Moderately Susceptible; S = Susceptible; VS = Very Susceptible. Reactions were determined based on historical and recent observations from test plots and in grower field across Arkansas. In general, these reactions would be expected under conditions that favor severe disease development including excessive nitrogen rates (most diseases) or low flood depth (blast).
Table prepared by Y. Wamishe, /Extension Plant Pathologist Herbicide Resistance of Rice Cultivar CLL16

Clearfield® (CL) rice is resistant to imidazolinone herbicides (WSSA Group 2), which control weeds by inhibiting the enzyme acetohydroxyacid synthase (AHAS), also called acetolactate synthase (ALS). CL rice was developed through mutagenesis of the ALS locus using traditional breeding techniques and is not considered genetically modified. The herbicide-resistance trait of this rice makes it particularly useful in regions where there is a need to control weedy rice and other tough grasses. Thus, the majority of rice cultivars planted in the southern United States are CL inbred or hybrid.

The plants of rice cultivar CLL16 have increased tolerance or resistance to AHAS-inhibiting herbicides, particularly imidazolinone herbicides. Thus, the plants of rice cultivar CL 142-AR are herbicide-tolerant or herbicide-resistant rice plants. An "herbicide-tolerant" or a "herbicide-resistant" rice plant is a rice plant that is tolerant or resistant to at least one herbicide at a level that would normally kill, or inhibit the growth of, a normal or wild-type rice plant. For the present invention, the terms "herbicide-tolerant" and "herbicide-resistant" are used interchangeably and are intended to have an equivalent meaning and an equivalent scope. Similarly, the terms "herbicide-tolerance" and "herbicide-resistance" are used interchangeably and are intended to have an equivalent meaning and an equivalent scope. Likewise, the terms "imidazolinone-tolerant" and "imidazolinone-resistant" are used interchangeably and are intended to be of an equivalent meaning and an equivalent scope as the terms "imidazolinone-tolerance" and "imidazolinone-resistance", respectively.

Accordingly, the present invention also provides rice seeds treated with an AHAS-inhibiting herbicide. AHAS-inhibiting herbicides include, without limitation, imidazolinone herbicide, a sulfonylurea herbicide, a triazolopyrimidine herbicide, a pyrimidinyloxybenzoate herbicide, a sulfonylamino-carbonyltriazolinone herbicide, and a mixture thereof. However, in preferred embodiments, the AHAS-inhibiting herbicide is an imidazolinone herbicide or a mixture of two or more imidazolinone herbicides. Suitable imidazolinone herbicides include, without limitation, PURSUIT (imazethapyr), CADRE (imazapic), RAPTOR (imazamox), SCEPTER (imazaquin), ASSERT (imazethabenz), ARSENAL (imazapyr), a derivative of any of the aforementioned herbicides, and a mixture of two or more of the aforementioned herbicides, for example, imazapyr/imazamox (ODYSSEY). More specifically, the imidazolinone herbicide can be selected from, but is not limited to, 2-(4-isopropyl-4-methyl-5-oxo-2-imidiazolin-2-yl)-nicotinic acid, [2-(4-isopropyl)-4-][methyl-5-oxo-2-imidazolin-2-yl)-3-quinolinecarboxylic]acid, [5-ethyl-2-(4-isopropyl-]4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, [2-(4-isopropyl-4-methyl-5-oxo-2-]imidazolin-2-yl)-5-methylnicotinic acid, and a mixture of methyl[6-(4-isopropyl-4-]methyl-5-oxo-2-imidazolin-2-yl)-m-toluate and methyl[2-(4-isopropyl-4-methyl-5-]oxo-2-imidazolin-2-yl)-p-toluate.

A wide variety of formulations can be employed for protecting plants from weeds, so as to enhance plant growth and reduce competition for nutrients. Customary formulations include, for example solutions, emulsions, suspensions, dusts, powders, pastes and granules. The use form depends on the particular intended purpose; in each case, it should ensure a fine and even distribution of the compound according to the invention.

The herbicide may be applied at pre-emergence, post-emergence, pre-planting or at planting to control weeds in areas surrounding the rice plants described herein. The herbicide and herbicide formulations can be applied in accordance with conventional methods, for example, by spraying, irrigation, dusting, or the like. In some embodiments, the herbicide is applied by contacting the rice seeds before sowing and/or after pregermination with an AHAS-inhibiting herbicide. In other embodiments, the herbicide is applied to the weeds and to the rice plant applied post-emergence, e.g., using over-the-top application.

An herbicide can be used by itself or an herbicide formulation can be used that contains other additives. The herbicide can also be used as a seed treatment. Additives that may be found in an herbicide formulation include other herbicides, detergents, adjuvants, spreading agents, sticking agents, stabilizing agents, or the like. The herbicide formulation can be a wet or dry preparation and can include, but is not limited to, flowable powders, emulsifiable concentrates and liquid concentrates. Such formulations are prepared in a known manner, for example by extending the active compound with auxiliaries suitable for the formulation of agrochemicals, such as solvents and/or carriers, emulsifiers, surfactants and dispersants, preservatives, antifoaming agents, anti-freezing agents, and also optionally colorants and/or binders and/or gelling agents.

Methods

This present invention provides methods for producing rice plants. In some embodiments, these methods involve planting a plurality of rice seeds provided herein under conditions favorable for the growth of rice plants.

The plants of rice cultivar CLL16 have increased resistance to AHAS-inhibiting herbicides, particularly imidazolinone herbicides, and thus find use in methods for controlling weeds. Accordingly, the present invention provides methods for controlling weeds in the vicinity of a rice plant of rice cultivar CLL16. The AHAS-inhibiting herbicide may be selected from the group consisting of an imidazolinone herbicide, a sulfonylurea herbicide, a triazolopyrimidine herbicide, a pyrimidinyloxybenzoate herbicide, a sulfonylamino-carbonyltriazolinone herbicide, or a mixture thereof. However, in preferred embodiments, the AHAS-inhibiting herbicide is an imidazolinone herbicide or a mixture of two or more imidazolinone herbicides.

The herbicide may be applied using any application method known in the art including, but not limited to, seed treatment, soil treatment, and foliar treatment. In some embodiments, the herbicide is applied by contacting the rice seeds with the herbicide. The term "contacting" signifies that the active ingredient of the herbicide is on the surface of the seed at the time of application, though a greater or lesser amount of the ingredient may penetrate into the seed, depending on the method of application. Suitable seed treatment techniques include, without limitation, seed dressing, seed coating, seed dusting, seed soaking, and seed pelleting. In some embodiments, the herbicide is applied to the seeds before sowing and/or after pregermination. Pregermination refers to a process in which seeds are sprouted in the absence of soil. Thus, the phrase "after pregermination" refers to the period of development after germination has occurred (i.e., the root penetrates through the seed coat).

In other embodiments, the herbicide is applied to the weeds and to the rice plant post-emergence, i.e., after the weeds and crop have emerged from the soil. These treatments either can be applied in a broadcast or directed fashion. Notably, for post-emergence applications it is often advantageous to combine the herbicide with a surfactant to facilitate maximum coverage of the weed with the solution. Additives found in an imidazolinone herbicide formulation include other herbicides, detergents, adjuvants, spreading agents, sticking agents, stabilizing agents, or the like. The herbicide formulation can be a wet or dry preparation and can include, but is not limited to, flowable powders, emulsifiable concentrates and liquid concentrates. The herbicide and herbicide formulations can be applied in accordance with conventional methods, for example, by spraying, irrigation, dusting, or the like.

For the methods of the present invention, the preferred amount or concentration of the herbicide is an "effective amount" or "effective concentration, i.e., an amount or concentration that is sufficient to kill or inhibit the growth of a similar, wild-type, rice plant, rice plant tissue, rice plant cell, or rice seed, but that said amount does not kill or inhibit as severely the growth of the herbicide-resistant plants, plant tissues, plant cells, and seeds of the present invention. Typically, the effective amount of an herbicide is an amount that is routinely used in agricultural production systems to kill weeds of interest. Such an amount is known to those of ordinary skill in the art. Herbicide application rates generally range from 0.1 g to 10 kg of the active ingredient per 100 kg of seed, preferably from 1 g to 5 kg per 100 kg of seed, in particular from 1 g to 2.5 kg per 100 kg of seed. The phrase "control of undesired vegetation" refers to the killing of weeds and/or otherwise retarding or inhibiting the normal growth of the weeds. Weeds, in the broadest sense, are understood as meaning all plants that grow in locations where they are undesired. The weeds may include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus*, and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus*, and *Apera*. In addition, the weeds of the present invention can include crop plants that are growing in an undesired location. For example, a volunteer soybean plant that is in a field that predominantly comprises rice plants can be considered a weed, if the soybean plant is undesired in the field of rice plants. Another example of a weed of the present invention is red rice, which is the same species as cultivated rice.

In these methods, the AHAS-inhibiting herbicide can be applied by any method known in the art including, but not limited to, seed treatment, soil treatment, and foliar treatment. Prior to application, the AHAS-inhibiting herbicide can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner (see, e.g., for review, U.S. Pat. No. 3,060,084, EP-A 707 445 (for liquid concentrates), Browning, "Agglomeration", Chemical Engineering, pp. 147-48 (Dec. 4, 1967); Perry's Chemical Engineer's Handbook, 4th Ed., McGraw-Hill, New York, pp. 8-57 (1963), and et seq.; PCT Publication No. WO 91/13546; U.S. Pat. Nos. 4,172,714; 4,144,050; 3,299,566; 3,920,442; 5,180,587; 5,232,701; and 5,208,030; G.B. Patent No. 2,095,558; Klingman, "Weed Control as a Science", John Wiley and Sons, Inc., New York (1961); Hance et al., Weed Control Handbook, 8th Ed., Blackwell Scientific Publications, Oxford (1989); Mollet, H., Grubemann, A., Formulation technology, Wiley VCH Verlag GmbH, Weinheim, Germany (2001); and D. A. Knowles, Chemistry and Technology of Agrochemical Formulations, Kluwer Academic Publishers (ISBN 0-7514-0443-8), Dordrecht (1998)), for example by extending the active compound with auxiliaries suitable for the formulation of agrochemicals, such as solvents and/or carriers, if desired, emulsifiers, surfactants and dispersants, preservatives, antifoaming agents, anti-freezing agents, for seed treatment formulation, also optionally colorants and/or binders and/or gelling agents.

Examples of suitable solvents are water, aromatic solvents (for example, Solvesso products, xylene), paraffins (for example, mineral oil fractions), alcohols (for example, methanol, butanol, pentanol, benzyl alcohol), ketones (for example, cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used. Examples of suitable carriers are ground natural minerals (for example, kaolins, clays, talc, chalk) and ground synthetic minerals (for example, highly disperse silica, silicates). Suitable emulsifiers are nonionic and anionic emulsifiers (for example, polyoxyethylene fatty alcohol ethers, alkylsulfonates and arylsulfonates). Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as, kerosene or diesel oil, furthermore coal tar oils and oils of vegetable or animal origin, aliphatic, cyclic and aromatic hydrocarbons, for example, toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example, dimethyl sulfoxide, N-methylpyrrolidone or water. Also anti-freezing agents such as glycerin, ethylene glycol, propylene glycol and bactericides such as can be added to the formulation. Suitable antifoaming agents are for example antifoaming agents based on silicon or magnesium stearate. Suitable preservatives are for example Dichlorophen and enzylalkoholhemiformal. Seed treatment formulations may additionally comprise binders and optionally colorants.

Binders can be added to improve the adhesion of the active materials on the seeds after treatment. Suitable binders are block copolymers EO/PO surfactants but also polyvinylalcohols, polyvinylpyrrolidones, polyacrylates, polymethacrylates, polybutenes, polyisobutylenes, polystyrene, polyethyleneamines, polyethyleneamides, polyethyleneimines (LUPASOL, POLYMIN), polyethers, polyurethans, polyvinylacetate, tylose and copolymers derived from these polymers.

Optionally, colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108. An example of a suitable gelling agent is carrageen (SATIAGEL).

Powders, materials for spreading, and dustable products can be prepared by mixing or concomitantly grinding the active substances with a solid carrier. Granules, for example, coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01% to 95% by weight, preferably from 0.1 to 90% by weight, of the AHAS-inhibiting herbicide. In this case, the AHAS-inhibiting herbicides are employed in a purity of 90% to 100% by weight, preferably 95% to 100% by weight (according to NMR spectrum). For seed treatment purposes, respective formulations can be diluted 2-10 fold leading to concentrations in the ready to use preparations of 0.01% to 60% by weight active compound by weight, preferably 0.1 to 40% by weight.

The AHAS-inhibiting herbicide can be used as such, in the form of their formulations or the use forms prepared therefrom, for example, in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the AHAS-inhibiting herbicide according to the invention. Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water. The active compound concentrations in the ready-to-use preparations can be varied within relatively wide ranges. In general, they are from 0.0001% to 10%, preferably from 0.01% to 1% per weight. The AHAS-inhibiting herbicide may also be used successfully in the ultra-low-volume process (ULV), it being possible to apply formulations comprising over 95% by weight of active compound, or even to apply the active compound without additives.

This present invention also provides methods for producing an herbicide-resistant rice plant. The methods involve crossing a first parent rice plant of cultivar CLL16 with a second parent rice plant, which optionally is not resistant to an herbicide or contains another desired trait such as insect resistance. In some embodiments, a breeding cross is made to introduce new genetics into the CLL16 progeny (as opposed to a self or a sib cross, made to select among existing genetic alleles). In these embodiments, a population of hybrid rice plants will be produced that, on average, derive 50% of their alleles from cultivar CLL16. The resulting first generation (F1) hybrid rice seeds may be harvested and used to grow plants that express a subset of characteristics from CLL16. Alternatively, a plant of this population may be selected and repeatedly selfed or sibbed with a rice cultivar resulting from successive filial generations. In other embodiments, both the first and second parent rice plants can come from the rice cultivar CLL16. However, advantageously, the rice cultivar is used in crosses with other, different, rice cultivars to produce F1 rice seeds and plants with superior characteristics. In some embodiments, the rice cultivar CLL16 is crossed with a second rice plant that is transgenic. Rice cultivar CLL16 may also be crossed with other species, including those of the family Graminaceae, and especially of the genera *Zea, Tripsacum, Croix, Schlerachne, Polytoca, Chionachne*, and *Trilobachne*, of the tribe Maydeae. See the section below titled "Breeding Methods" for a detailed description of breeding techniques that may utilized with the present invention.

In some embodiments, a CLL16 progeny plant is selected that has molecular markers, morphological characteristics, and/or physiological characteristics in common with CLL16 (e.g., those listed in Table 2). Techniques such as RFLP-enhanced selection, genetic marker enhanced selection (e.g., SSR markers), and the making of double haploids may be utilized to identify progeny that share particular traits with CLL16.

Further, this invention provides methods for introducing a desired trait into rice cultivar CLL16. This may be accomplished using traditional breeding methods, such as backcrossing. Here, rice cultivar CLL16 is crossed with a second rice line expressing the desired trait and progeny with both the desired trait and characteristics of CLL16 are selected and crossed. These steps are repeated until plants with both the desired trait and essentially all the physiological and morphological characteristics of CLL16 have been produced.

Alternatively, the desired trait may be introduced by transforming the rice cultivar with a transgene. The transgene may confer at least one trait selected from the following: herbicide resistance; insect resistance; resistance to bacterial, fungal, or viral disease; modified fatty acid metabolism; modified carbohydrate metabolism; and male sterility. See the section below titled "Transformation Methods" for a detailed description of transformation techniques that may utilized with the present invention. The transgenic cultivar produced by these methods may be crossed with another cultivar to produce a new transgenic cultivar. Alternatively, the transgene incorporated by these methods could be moved into another cultivar using traditional backcrossing techniques.

Optionally, any of the disclosed methods may further comprise additional steps involving producing rice seed from the resulting rice plants and/or planting the rice seed.

The present invention encompasses all plants, or parts thereof, produced by the methods described herein, as well as the seeds produced by these plants. Further, any plants derived from rice cultivar CLL16 or produced from a cross using cultivar CLL16 are provided. This includes genetic variants, created either through traditional breeding methods or through transformation, as well as plants produced in a male-sterile form. Notably, this includes gene-converted plants developed by backcrossing. Any of the seeds, plants, or plant parts provided may be utilized for human food, livestock feed, and as a raw material in industry.

The present invention also encompasses progeny of rice cultivar CLL16 comprising a combination of at least two CLL16 traits selected from those listed in the Tables and Detailed Description of the Invention, wherein the progeny rice plant is not significantly different from CLL16 for said traits, as determined at the 5% significance level when grown in the same environment. One of skill in the art knows how to compare a trait between two plant varieties to determine if there is a significant difference between them (Fehr and Walt, Principles of Cultivar Development, pp. 261-286 (1987)). Molecular markers or mean trait values may be used to identify a plant as progeny of CLL16. Alternatively, progeny may be identified through their filial relationship with rice cultivar CLL16 (e.g., as being within a certain number of breeding crosses of rice cultivar CLL16). For example, progeny produced by the methods described herein may be within 1, 2, 3, 4, or 5 breeding crosses of rice cultivar CLL16.

Tissue Culture

The present invention provides tissue cultures of regenerable cells or protoplasts produced from rice cultivar CLL16. As is well known in the art, tissue culture of rice can be used for the in vitro regeneration of a rice plant. Thus, such cells and protoplasts may be used to produce plants having the physiological and morphological characteristics of rice cultivar CLL16. The rice plants regenerated by these methods are also encompassed by the present invention.

As used herein, the term "tissue culture" describes a composition comprising isolated cells or a collection of such cells organized into parts of a plant. Exemplary tissues for culture include protoplasts, calli, plant clumps, and plant cells that can be grown in culture, or parts of plants, such as embryos, pollen, flowers, seeds, pods, leaves, stems, roots, root tips, and anthers. Culture of various rice tissues and regeneration of plants therefrom is well known in the art.

Breeding Methods

The goal of rice breeding is to develop new, superior rice cultivars and hybrids. A superior cultivar is produced when a new combination of desirable traits is formed within a single plant variety. Desirable traits may include higher seed yield, resistance to diseases and insects, better stems and roots, tolerance to low temperatures, and better agronomic characteristics or grain quality.

The breeding methods used with the present invention may involve a single-seed descent procedure, in which one seed per plant is harvested and used to plant the next generation. Alternatively, the methods may utilize a multiple-seed procedure, in which one or more seeds harvested from each plant in a population is threshed together to form a bulk which is used to plant the next generation.

Use of rice cultivar CLL16 in any plant breeding method is encompassed by the present invention. The choice of a breeding or selection method will depend on several factors, including the mode of plant reproduction, the heritability of the trait(s) being improved, and the type of cultivar used commercially (e.g., F1 hybrid cultivar, pureline cultivar). Popular selection methods include pedigree selection, modified pedigree selection, mass selection, recurrent selection, backcrossing, or a combination thereof.

Pedigree selection is commonly used for the improvement of self-pollinating crops. Two parents are crossed to produce an F1 population. An F2 population is produced by selfing one or several F1's. Selection of the best individuals may begin in the F2 population; then, beginning in the F3 generation, the best individuals in the best families are selected. Replicative testing of families can begin in the F4 generation to make selection of traits with low heritability more effective. At an advanced stage of inbreeding (e.g., F6 or F7), the best lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population, which is often subjected to additional cycles of selection.

Backcrossing is commonly used to transfer genes for highly heritable traits into a desirable homozygous cultivar or inbred line. The term "backcrossing" refers to the repeated crossing of hybrid progeny back to one of the parental plants, referred to as the recurrent parent. The plant that serves as the source of the transferred trait is called the donor parent. After the initial cross, individuals possessing the transferred trait are selected and repeatedly crossed to the recurrent parent. The resulting plant is expected to have the attributes of the recurrent parent along with the trait transferred from the donor parent.

Transformation Methods

As is noted above, the present invention provides plants and seeds of rice cultivar CLL16 in which additional traits have been transferred. While such traits may be selected for using traditional breeding methods, they may also be introduced as transgenes. "Transgenes" include both foreign genes and additional or modified versions of native genes. Plants can be genetically engineered to have a wide variety of traits of agronomic interest including, without limitation, male sterility, waxy starch, herbicide resistance, resistance for bacterial, fungal, or viral disease, insect resistance, male fertility, enhanced nutritional quality, industrial usage, yield stability, and yield enhancement. Many examples of genes that confer such traits have been described in the literature and are well known in the art. For example, the transgene may confer resistance to an additional herbicide selected from the group consisting of: glyphosate, sulfonylurea, imidazolinone, dicamba, glufosinate, phenoxy proprionic acid, L-phosphinothricin, cyclohexone, cyclohexanedione, triazine, 2,4-Dichlorophenoxyacetic acid, hydroxyphenylpyruvate dioxygenase (HPPD) inhibitors, and benzonitrile.

Transgenes are typically introduced in the form of an expression vector. As used herein, an "expression vector" is DNA comprising a gene operatively linked to a regulatory element (e.g., a promoter). The expression vector may contain one or more such gene/regulatory element combinations. The expression vector may also include additional sequences, such as a signal sequence or a tag, that modify the protein produced by the transgene. The vector may be a plasmid, and can be used alone or in combination with other plasmids.

Expression vectors include at least one genetic marker operably linked to a regulatory element (e.g., a promoter) that allows transformed cells containing the vector to be recovered by selection. In some embodiments, negative selection (i.e., inhibiting growth of cells that do not contain the selectable marker gene) it utilized. Negative selection markers include, for example, genes that result in detoxification of a chemical agent (e.g., an antibiotic or an herbicide) and genes that result in insensitivity to an inhibitor. Exemplary negative selection genes include neomycin phosphotransferase II (nptII), hygromycin phosphotransferase, gentamycin acetyl transferase, streptomycin phosphotransferase, and aminoglycoside-3'-adenyl transferase. In other embodiments, positive selection (i.e., screening for the product encoded by a reporter gene) is utilized. Exemplary reporter genes include β-glucuronidase, β-galactosidase, luciferase, chloramphenicol acetyltransferase, and Green Fluorescent Protein (GFP).

Transgene expression is typically driven by operably linking the transgene to a promoter within the expression vector. However, other regulatory elements may also be used to drive expression, either alone or in combination with a promoter. As used herein, a "promoter" is a region of DNA upstream of a transcription start site that is involved in recognition and binding of RNA polymerase for transcription initiation. Any class of promoter may be selected to drive the expression of a transgene. For example, the promoter may be "tissue-specific", "cell type-specific", "inducible", or "constitutive". Those of skill in the art know how to select a suitable promoter based the particular circumstances and genetic engineering goals.

Methods for producing transgenic plants are well known in the art. General descriptions of plant expression vectors, reporter genes, and transformation protocols can be found in Gruber, et al., "Vectors for Plant Transformation", in *Methods in Plant Molecular Biology & Biotechnology* in Glich, et al., (Eds. pp. 89-119, CRC Press, 1993). General methods of culturing plant tissues are provided for example by Maki, et al., "Procedures for Introducing Foreign DNA into Plants" in *Methods in Plant Molecular Biology & Biotechnology*, Glich, et al., (Eds. pp. 67-88 CRC Press, 1993); and by Phillips, et al., "Cell-Tissue Culture and In-Vitro Manipulation" in *Corn & Corn Improvement*, 3rd Edition; Sprague, et al., (Eds. pp. 345-387 American Society of Agronomy Inc., 1988). Methods of introducing expression vectors into plant tissue include direct gene transfer methods, such as microprojectile-mediated delivery, DNA injection, and electroporation, as well as the direct infection or co-cultivation of plant cells with *Agrobacterium tumefaciens*, described for example by Horsch et al., *Science*, 227:1229 (1985). Descriptions of *Agrobacterium* vector systems and methods for *Agrobacterium*-mediated gene transfer are provided by Gruber, et al., supra.

REFERENCES

Moldenhauer, K. A. K., F. N. Lee, J. L. Bernhardt, R. J. Norman, N. A. Slaton, C. E. Wilson, M. M. Anders, R. D. Cartwright, and M. M. Blocker. 2007. Registration of 'Wells' rice. Crop Sci. 47:442-443.

Moldenhauer, K. A. K., J. W. Gibbons, F. N. Lee, J. L. Bernhardt, C. E. Wilson, Jr., R. D. Cartwright, R. J. Norman, M. M. Blocker, D. K. Ahrent, V. A. Boyett, J. M Bulloch, and E. Castaneda. 2009. 'Taggart', high yielding large kernel long-grain rice variety. In R. J. Norman, J. F. Meullenet and K. A. K. Moldenhauer (eds.) Rice Research Studies 2008. University of Arkansas Agricultural Experiment Station Research Series 571. pp. 68-73.

Webb, B. D., C. N. Bollich, H. L. Carnahan, K. A. Kuenzel., and K. S. McKenize. 1985. Utilization characteristics and qualities of United States rice. p. 25-35. In: Rice grain quality and marketing. IRRI, Manila, Philippines

DEPOSIT INFORMATION

A deposit of the University of Arkansas Division of Agriculture Rice Research and Extension Center proprietary rice cultivar CLL16 disclosed above and recited in the appended claims has been made with the American Type Culture Collection (ATCC), 10801 University Boulevard, Manassas, Va. 20110. The date of deposit was Sep. 28, 2020. The deposit of 2,500 seeds was taken from the same deposit maintained by the University of Arkansas Division of Agriculture Rice Research and Extension Center (2900 Hwy 130 E., Stuttgart, Ark. 72160) since prior to the filing date of this application. All restrictions will be irrevocably removed upon granting of a patent, and the deposit is intended to meet all of the requirements of 37 C.F.R. §§ 1.801-1.809. The ATCC Accession Number is PTA-126847 The deposit will be maintained in the depository for a period of thirty years, or five years after the last request, or for the enforceable life of the patent, whichever is longer, and will be replaced as necessary during that period.

What is claimed is:

1. A rice seed of the cultivar CLL16, a representative sample of seed of said cultivar having been deposited under ATCC Accession No. PTA-126847.

2. The rice seed of claim 1, wherein said seed is treated with an agronomically acceptable seed treatment composition.

3. The rice seed of claim 2, wherein said seed is treated with an acetohydroxyacid synthase (AHAS)-inhibiting herbicide.

4. The rice seed of claim 3, wherein said AHAS-inhibiting herbicide is selected from the group consisting of imidazolinone herbicides, sulfonylurea herbicides, triazolopyrimidine herbicides, pyrimidinyloxybenzoate herbicides, sulfonylamino-carbonyltriazolinone herbicides, and combinations or mixtures thereof.

5. The rice seed of claim 3, wherein said AHAS-inhibiting herbicide is an imidazolinone herbicide or a mixture of two or more imidazolinone herbicides.

6. The rice seed of claim 5, wherein the imidazolinone herbicide is selected from the group consisting of 2-(4-isopropyl-4-methyl-5-oxo-2-imidazolin-2-yl)-nicotinic acid, 2-(4-isopropyl-4-methyl-5-oxo-2-imidazolin-2-yl)-3-quinolinecarboxylic acid, 5-ethyl-2-(4-isopropyl-4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, 2-(4-isopropyl-4-methyl-5-oxo-2-imidazolin-2-yl)-5-methylnicotinic acid, mixtures of methyl-6-(4-isopropyl-4-methyl-5-oxo-2-imidazolin-2-yl)-m-toluate and methyl-2-(4-isopropyl-4-methyl-5-oxo-2-imidazolin-2-yl)-p-toluate, imazapyr, imazapic, imazethapyr, imazamox, imazamethabenz, and imazaquin herbicides and combinations or mixtures thereof.

7. A rice plant, or a part thereof, produced by growing the seed of claim 1.

8. A rice plant, or a part thereof, having all of the physiological and morphological characteristics of the rice plant of claim 7.

9. Pollen or an ovule of the plant of claim 7.

10. A method for producing rice plants, said method comprising planting a plurality of rice seeds as recited in claim 1 under conditions favorable for the growth of rice plants.

11. The method of claim 10, further comprising the step of producing rice seed from the resulting rice plants.

12. A rice seed produced by the method of claim 11.

13. A method for combating undesired vegetation or controlling weeds in the vicinity of a rice plant of rice cultivar CLL16, a representative sample of seed of said cultivar having been deposited under ATCC Accession No. PTA-126847, said method comprising contacting the rice seed of claim 1 with an AHAS-inhibiting herbicide before sowing and/or after pregermination.

14. The method of claim 13, wherein said AHAS-inhibiting herbicide is selected from the group consisting of imidazolinone herbicides, sulfonylurea herbicides, triazolopyrimidine herbicides, pyrimidinyloxybenzoate herbicides, sulfonylamino-carbonyltriazolinone herbicides, or combinations and mixtures thereof.

15. The method of claim 14, wherein said AHAS-inhibiting herbicide is an imidazolinone herbicide or a mixture of two or more imidazolinone herbicides.

16. A method for combating undesired vegetation or controlling weeds in the vicinity of a rice plant of rice cultivar CLL16, comprising applying an effective amount of at least one AHAS-inhibiting herbicide to the weeds and to the rice plant, a representative sample of seed of said cultivar having been deposited under ATCC Accession No. PTA-126847.

17. The method of claim 16, wherein said AHAS-inhibiting herbicide is selected from the group consisting of imidazolinone herbicides, sulfonylurea herbicides, triazolopyrimidine herbicides, pyrimidinyloxybenzoate herbicides, sulfonylamino-carbonyltriazolinone herbicides, and combinations or mixtures thereof.

18. The method of claim 17, wherein said AHAS-inhibiting herbicide is an imidazolinone herbicide or a mixture of two or more imidazolinone herbicides.

19. The method of claim 17, wherein said imidazolinone herbicide is selected from the group consisting of 2-(4-isopropyl-4-methyl-5-oxo-2-imidazolin-2-yl)-nicotinic acid, 2-(4-isopropyl-4-methyl-5-oxo-2-imidazolin-2-yl)-3-quinolinecarboxylic acid, 5-ethyl-2-(4-isopropyl-4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, 2-(4-isopropyl-4-methyl-5-oxo-2-imidazolin-2-yl)-5-methylnicotinic acid, mixtures of methyl-6-(4-isopropyl-4-methyl-5-oxo-2-imidazolin-2-yl)-m-toluate and methyl-2-(4-isopropyl-4-methyl-5-oxo-2-imidazolin-2-yl)-p-toluate, imazapyr, imazapic, imazethapyr, imazamox, imazamethabenz, and imazaquin herbicides and combinations or mixtures thereof.

20. A tissue culture of regenerable cells or protoplasts produced from the rice plant, or a plant part of claim 7.

21. The tissue culture of claim 20, wherein said cells or protoplasts are produced from a tissue selected from the group consisting of embryos, meristematic cells, pollen, ovules, leaves, anthers, roots, root tips, pistils, cotyledon, hypocotyl, glumes, panicles, flowers, seeds, and stems.

22. A rice plant regenerated from the tissue culture of claim 20, said rice plant having all of the morphological and physiological characteristics of a rice plant of rice cultivar CLL16, a representative sample of seed of said cultivar having been deposited under ATCC Accession No. PTA-126847.

23. A method for producing an herbicide-resistant rice hybrid plant, said method comprising crossing a first parent rice plant with a second parent rice plant, wherein the first parent rice plant is the rice plant of claim 7, and optionally wherein the second parent rice plant is not resistant to an herbicide.

24. The method of claim 23, further comprising selecting for a progeny rice plant that is resistant to at least one AHAS-inhibiting herbicide.

25. The method of claim 24, wherein said AHAS-inhibiting herbicide is an imidazolinone herbicide or a mixture of two or more imidazolinone herbicides.

26. An herbicide-resistant rice plant or plant part produced by the method of claim 23.

27. The method of claim 23, further comprising the step of producing rice seed from the resulting rice plants.

28. The method of claim 23, wherein the second parent rice plant is transgenic.

29. A method comprising transforming the rice plant of claim 7 or cell thereof with a transgene, wherein the transgene confers at least one trait selected from the group consisting of: herbicide resistance; insect resistance; resistance to bacterial, fungal, or viral disease; modified fatty acid metabolism; modified carbohydrate metabolism; and male sterility.

30. A rice plant or part thereof, or rice seed, produced by the method of claim 29.

31. A method of introducing a desired trait into rice cultivar CLL16, a representative sample of seed of said cultivar having been deposited under ATCC Accession No. PTA-126847, said method comprising the steps of:
   (a) crossing plants as recited in claim 7 with plants of another rice line expressing the desired trait, to produce progeny plants;
   (b) selecting progeny plants that express the desired trait, to produce selected progeny plants;
   (c) crossing the selected progeny plants with plants of rice cultivar CLL16 a representative sample of seed of said cultivar having been deposited under ATCC Accession No. PTA-126847N to produce new progeny plants;
   (d) selecting new progeny plants that express the desired trait; and
   (e) repeating steps (c) and (d) three or more times in succession, to produce selected higher generation backcross progeny plants that express the desired trait.

32. The method of claim 31, wherein the desired trait is selected from the group consisting of: herbicide resistance traits; insect resistance traits; traits of resistance to bacterial, fungal, or viral disease; modified fatty acid metabolism traits; modified carbohydrate metabolism traits; and male sterility traits.

33. The method of claim 32, wherein the desired trait is herbicide resistance to an AHAS-inhibiting herbicide selected from the group consisting of imidazolinone herbicides, sulfonylurea herbicides, triazolopyrimidine herbicides; pyrimidinyloxybenzoate herbicides, sulfonylaminocarbonyltriazolinone herbicides, and combinations or mixtures thereof.

* * * * *